United States Patent [19]

Reiser et al.

[11] Patent Number: 4,603,140
[45] Date of Patent: Jul. 29, 1986

[54] SUBSTITUTED AZOLYLALKYL-T-BUTYL-KETONES AND -CARBINOLS

[75] Inventors: Wolf Reiser, Wuppertal; Karl H. Büchel, Burscheid; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 736,894

[22] Filed: May 22, 1985

Related U.S. Application Data

[63] Continuation of Ser. No. 526,929, Aug. 26, 1983, abandoned.

[30] Foreign Application Priority Data

Sep. 18, 1982 [DE] Fed. Rep. of Germany ....... 3234627

[51] Int. Cl.$^4$ .................. A01N 43/50; A01N 43/653; C07D 233/60; C07D 249/08
[52] U.S. Cl. ................................ 514/383; 514/184; 514/397; 548/101; 548/262; 548/341
[58] Field of Search .................. 548/101, 262, 341; 514/184, 383, 397

[56] References Cited

U.S. PATENT DOCUMENTS 4,243,405  1/1981  Balasubramanyan et al. ..... 548/101

FOREIGN PATENT DOCUMENTS

| | | | |
|---|---|---|---|
| 0016323 | 10/1980 | European Pat. Off. ............ | 548/262 |
| 0032200 | 7/1981 | European Pat. Off. ............ | 548/262 |
| 0031911 | 7/1981 | European Pat. Off. ............ | 548/262 |
| 2407143 | 8/1975 | Fed. Rep. of Germany ...... | 548/262 |
| 2737489 | 3/1978 | Fed. Rep. of Germany ...... | 548/262 |
| 2951163 | 7/1981 | Fed. Rep. of Germany ...... | 548/262 |
| 2951164 | 7/1981 | Fed. Rep. of Germany ...... | 548/262 |
| 1464224 | 2/1977 | United Kingdom ................ | 548/262 |

*Primary Examiner*—Alton D. Rollins
*Attorney, Agent, or Firm*—Sprung Horn Kramer & Woods

[57] ABSTRACT

Novel substituted azolylalkyl-t-butyl-ketones and -carbinols of the formula

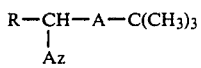

in which
   Az is imidazol-1-yl or 1,2,4-triazol-1-yl,
   A is the carbonyl group or the hydroxymethylene group, and
   R is optionally substituted cycloalkylalkyl or cycloalkenylalkyl, and plant-tolerated addition products thereof with acids and metal salts, which are fungicidally active and are also useful as intermediates in making other fungicides.

7 Claims, No Drawings

SUBSTITUTED AZOLYLALKYL-T-BUTYL-KETONES AND -CARBINOLS

This is a continuation of application Ser. No. 526,929, filed Aug. 26, 1983, abandoned.

The invention relates to new substituted azolylalkyl-t-butyl-ketones and -carbinols, a process for their preparation and their use as plant protection agents and as intermediates for the synthesis of further plant protection agents.

It has already been disclosed that certain substituted azolylalkyl-t-butyl-ketones and -carbinols, such as, for example, 1-(2,4-dichlorophenoxy)-3,3-dimethyl-1-(1,2,4-triazol-1-yl)-butan-2-one or 4,4-bis-(chloromethyl)-1-phenyl-1-(1,2,4-triazol-1-yl)-pentan-3-one or 2,2-dimethyl-1-fluoro-5-phenyl-4-(1,2,4-triazol-1-yl)-pentan-3-ol or 5-(3,4-dichlorophenyl)-2,2-dimethyl-1-fluoro-4-(1,2,4-triazol-1-yl)-pentan-3-ol, possess fungicidal activity (see DE-OS (German Published Specification) No. 2,407,143, DE-OS (German Published Specification) No. 2,951,164 and DE-OS (German Published Specification) No. 2,951,163).

However, the action of these azoles derivatives is not always completely satisfactory in certain fields of indication, in particular when low amounts and concentrations are used.

New substituted azolylalkyl-t-butyl-ketones and -carbinols of the general formula (I)

in which
Az represents imidazol-1-yl or 1,2,4-triazol-1-yl,
A represents the carbonyl group or the hydroxymethylene group and
R represents optionally substituted cycloalkylalkyl or cycloalkenylalkyl, and their plant-tolerated acid addition salts and metal salt complexes have been found.

Furthermore, it has been found that the substituted azolylalkyl-t-butyl-ketones of the general formula are obtained if azolylmethyl-t-butyl-ketones of the formula (II)

in which Az has the meaning given above, are reacted with an alkylating agent of the general formula (III)

in which
R has the meaning given above and
Z represents an electron-attracting leaving group, in the presence of a base and in the presence of an organic diluent, or in an aqueous-organic two-phase system in the presence of a phase-transfer catalyst and, if required, the resulting keto compounds (wherein, in formula (I), the symbol A represents the CO group) are reduced, by known methods, to the corresponding carbinols (wherein, in formula (I), the symbol A represents the CH(OH) group).

If required, an adduct of the compounds according to the invention, of the formula (I), with an acid or a metal salt can then be formed.

The new azolylalkyl-t-butyl-ketones and -carbinols of the formula (I) possess powerful fungicidal properties, and can therefore be used as plant protection agents.

Surprisingly, the substituted azolylalkyl-t-butyl-ketones and -carbinols according to the invention exhibit better fungicidal activity than the azoles 1-(2,4-dichlorophenoxy)-3,3-dimethyl-1-(1,2,4-triazol-1-yl)-butan-2-one or 4,4-bis-(chloromethyl)-1-phenyl-1-(1,2,4-triazol-1-yl)-pentan-3-one or 2,2-dimethyl-1-fluoro-5-phenyl-4-(1,2,4-triazol-1-yl)-pentan-3-ol or 5-(3,4-dichlorophenyl)-2,2-dimethyl-1-fluoro-4-(1,2,4-triazol-1-yl)-pentan-3-ol, which are known from the prior art and are similar compounds chemically and in terms of their action.

Furthermore, the substituted azolylalkyl-t-butyl-ketones and -carbinols according to the invention, of the formula (I), are interesting intermediate products for the preparation of further plant protection active compounds. Thus, for example, using known processes, keto compounds according to the invention can be converted with hydroxylamine or its derivatives or with hydrazines to the corresponding oximes and hydrazones. Furthermore, carbinols according to the invention can be converted with alkylating agents or acylating agents to the corresponding ethers and esters.

The substances according to the invention thus represent a valuable enrichment of the prior art.

Formula (I) gives a general definition of the substituted azolylalkyl-t-butyl-ketones and -carbinols according to the invention. In this formula, Az and A preferably have the meaning given in the definition of the invention, R preferably represents cycloalkylalkyl and cycloalkenylalkyl, each of which has 3 to 9 carbon atoms in the cycloalkyl or cycloalkenyl part and up to 4 carbon atoms in each alkyl part and is optionally monosubstituted to pentasubstituted by identical or different substituents, suitable substituents being: alkyl or alkoxy having up to 4 carbon atoms or halogen, in particular fluorine, chlorine or bromine.

Particularly preferred compounds of the formula (I) are those in which

Az and A have the meaning given in the definition of the invention and

R represents cyclobutylmethyl, cyclopentylmethyl, cyclohexylmethyl, cyclohexenylmethyl, cyclohexadienylmethyl, cycloheptylmethyl, cycloheptenylmethyl or cyclopropylmethyl which is optionally monosubstituted to trisubstituted by identical or different substituents from amongst methyl, methoxy, ethyl or chlorine.

In addition to the compounds mentioned in the preparation examples, the following compounds of the general formula (I) may be mentioned individually:

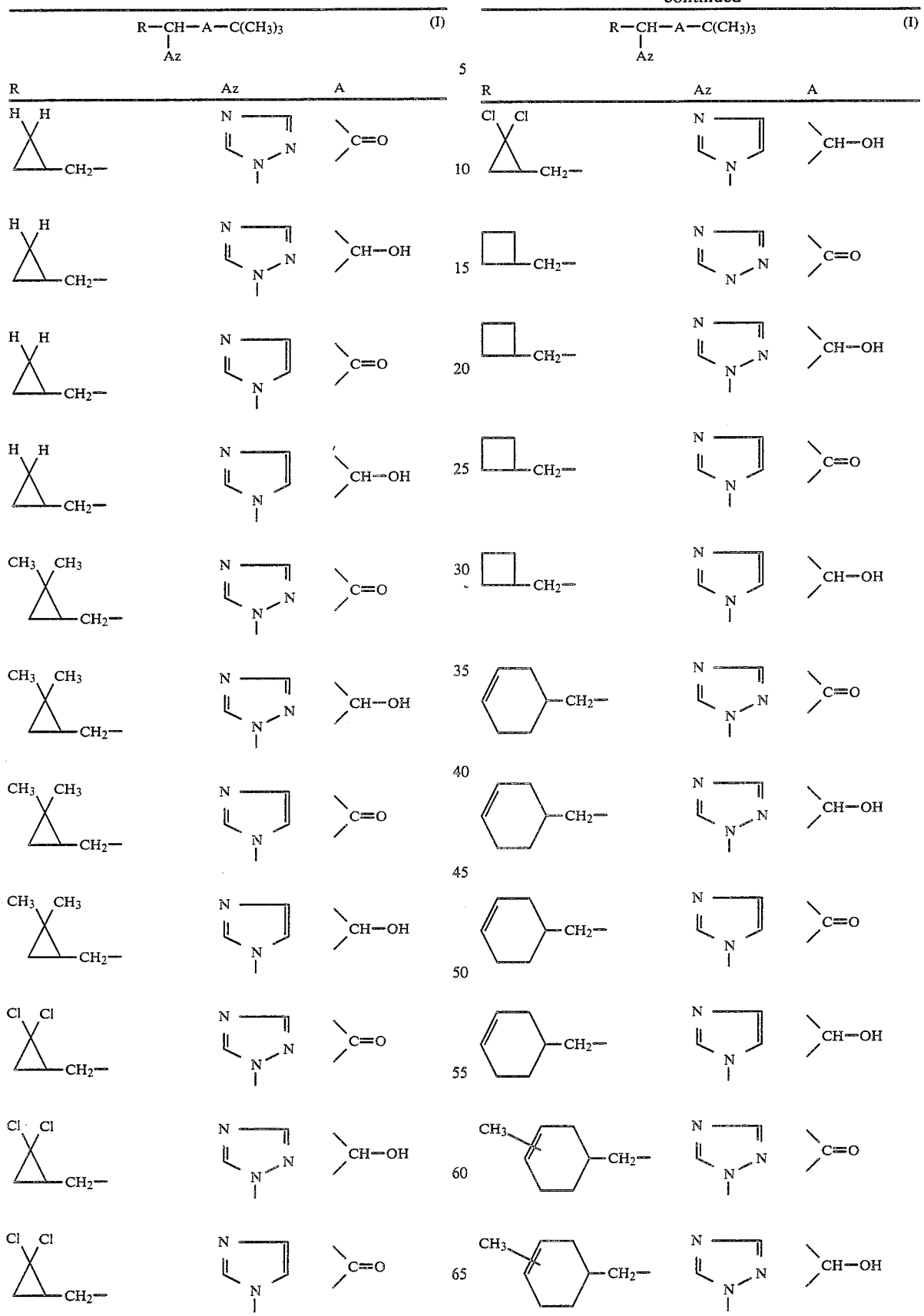

4,603,140
-continued
$$R-CH-A-C(CH_3)_3 \quad (I)$$
$$\quad\quad |$$
$$\quad\quad Az$$
| R | Az | A |
|---|----|---|
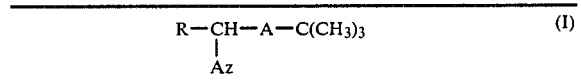
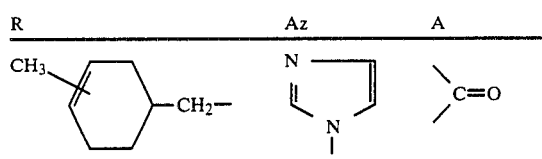
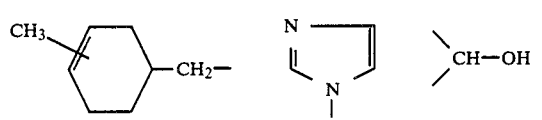
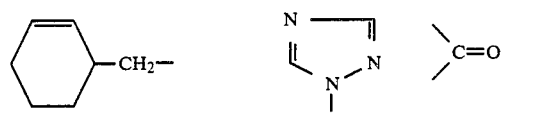
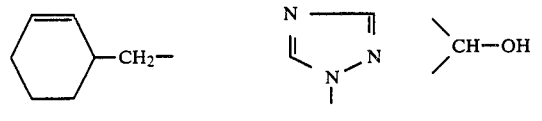
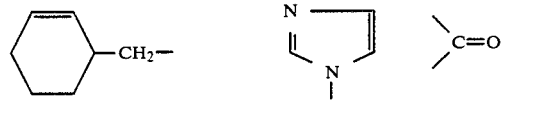
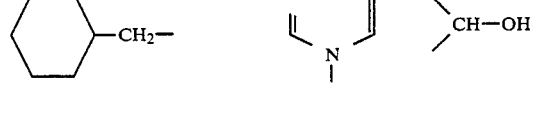
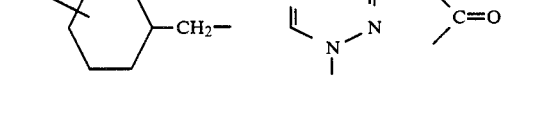
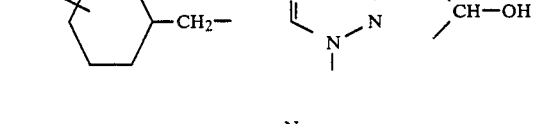
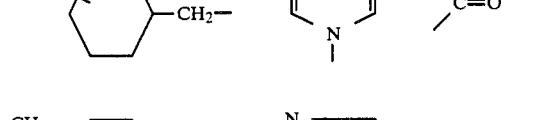
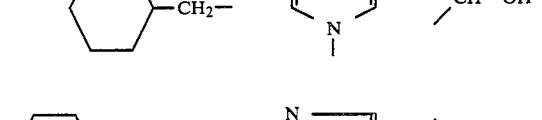
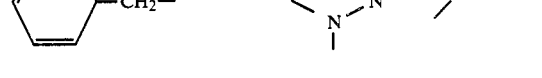
-continued
$$R-CH-A-C(CH_3)_3 \quad (I)$$
$$\quad\quad |$$
$$\quad\quad Az$$
| R | Az | A |
|---|----|---|
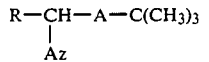
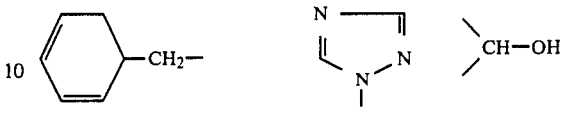
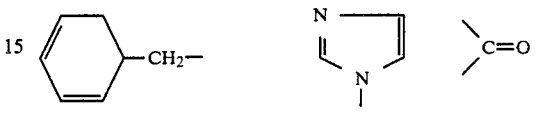
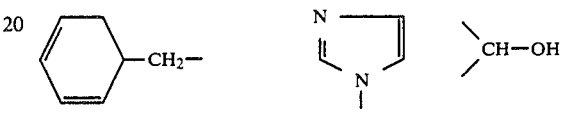
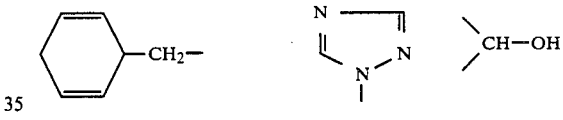
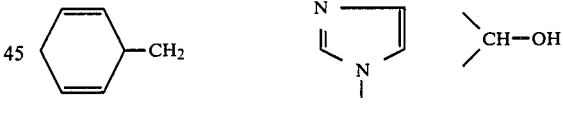
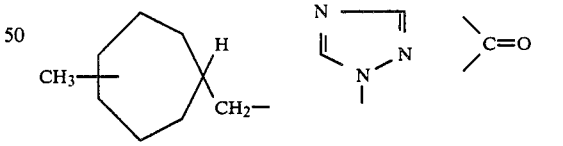
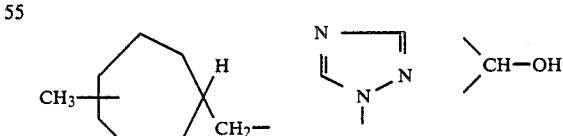
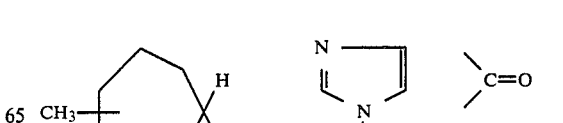
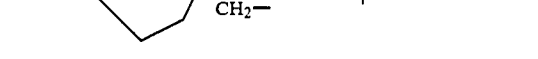

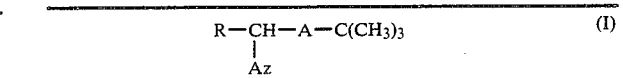
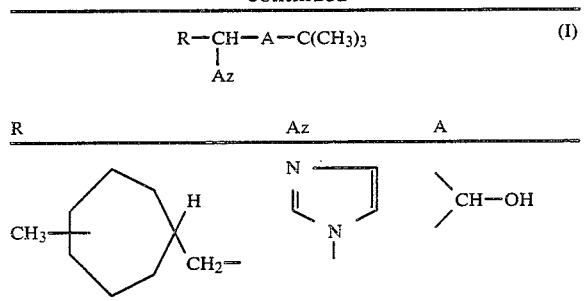
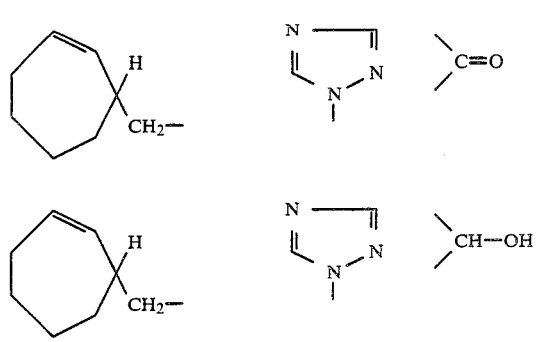
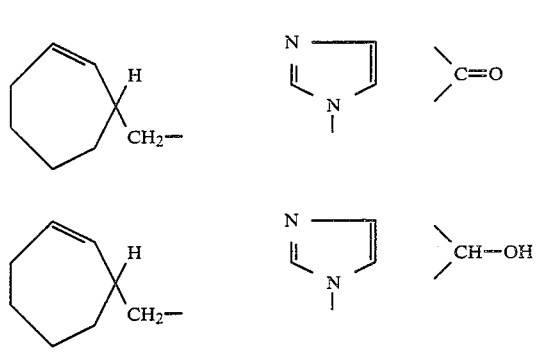
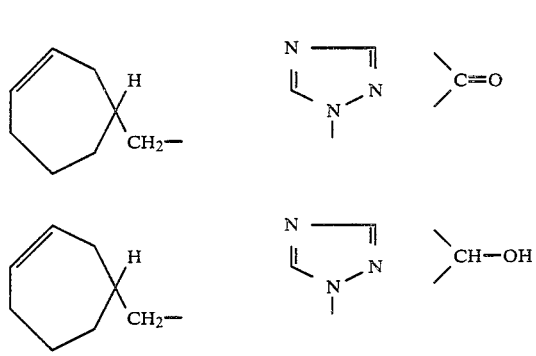
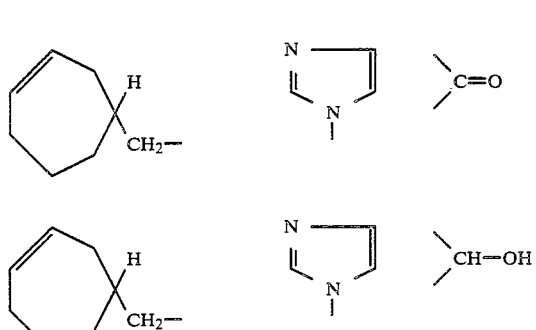
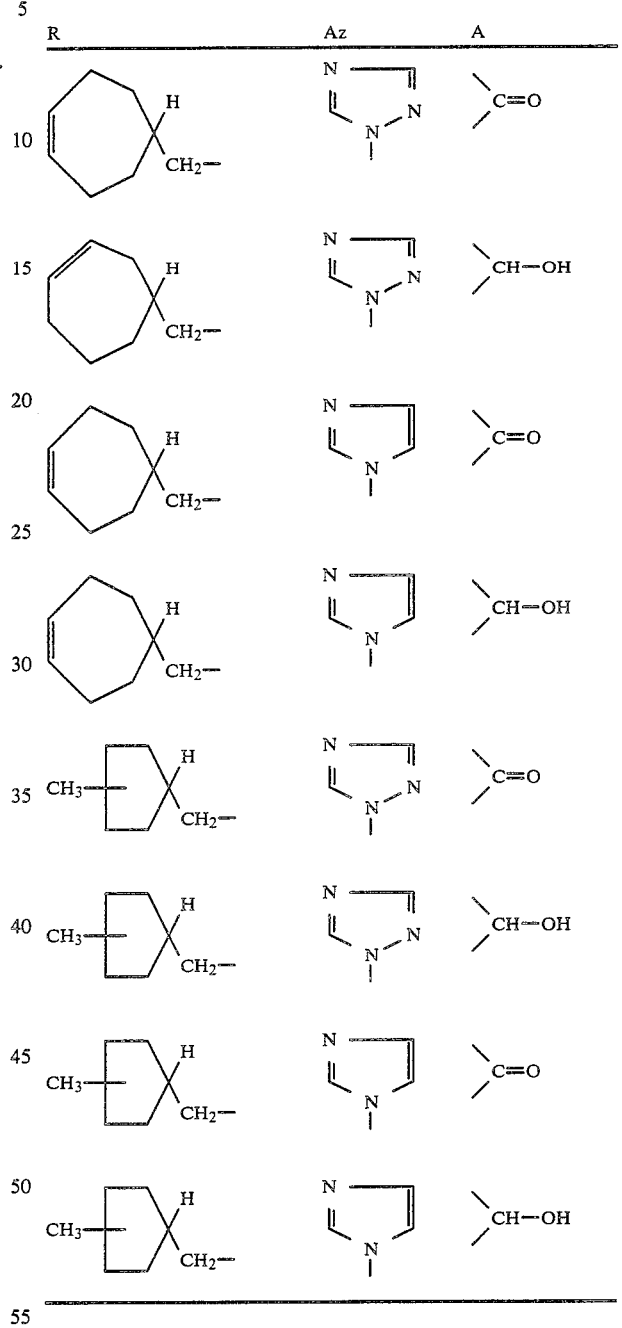
If, for example, 3,3-dimethyl-1-(1,2,4-triazol-1-yl)-butan-2-one and bromomethylcyclohexane are used as starting materials, the course of the reaction of the process according to the invention can be represented by the following equation:
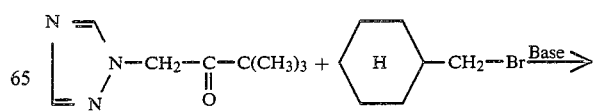

-continued

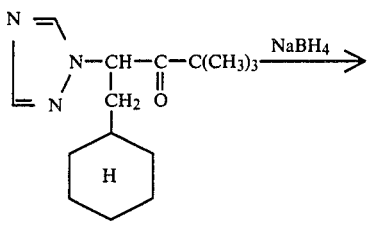

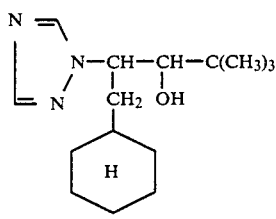

Formula (II) gives a general definition of the azolylmethyl-t-butyl-ketones required as starting materials for carrying out the process according to the invention. In this formula, Az preferably has the meaning given in the definition of the invention.

The azolylmethyl-t-butyl-ketones of the formula (II) are known (see DE-OS (German Published Specification) No. 2,431,407 and DE-OS (German Published Specification) No. 2,906,061 and can be obtained in the manner described if halogenoketones, such as, for example, chloro- or bromopinacol is reacted with imidazole or 1,2,4-triazole in the presence of an acid-binding agent, preferably in the presence of calcium carbonate or triethylamine, in a polar solvent (for example acetonitrile) in the temperature range between 60° and 120° C.

Formula (III) gives a general definition of the alkylating agents furthermore to be used as starting materials for the process according to the invention. In this formula, R preferably represents those radicals which have already been mentioned in connection with the description of the substances according to the invention, of the formula (I), as being preferred for these substituents. Z preferably represents an electron-attracting leaving group such as, for example, halogen, such as chlorine, bromine or iodine, p-methylphenylsulphonyloxy, or the group —O—SO$_2$—OR' or N$^\oplus$(R')$_3$, wherein R' represents alkyl having up to 4 carbon atoms, phenyl or tolyl.

The alkylating agents of the formula (III) are generally known compounds of organic chemistry.

Suitable diluents for the reaction according to the invention are inert organic solvents. These preferably include aromatic hydrocarbons, such as benzene, toluene or xylene; halogenated hydrocarbons, such as methylene chloride, carbon tetrachloride, chloroform or chlorobenzene; esters, such as ethyl acetate; formamides, such as dimethylformamide; and dimethylsulphoxide.

The reaction according to the invention is carried out in the presence of a base. In this reaction, it is possible to use all customary organic and, in particular, inorganic bases, such as, preferably, alkali metal hydroxides or alkali metal carbonates, sodium hydroxide and potassium hydroxide being mentioned as examples.

In carrying out the process according to the invention, the reaction temperatures can be varied within a relatively wide range. In general, the reaction is carried out at between 0° and 120° C., preferably between 20° and 100° C.

In carrying out the process according to the invention, 1 to 1.2 mols of alkylating agent of the formula (III) are preferably employed per mol of triazolylmethyl-tert.-butyl-ketone of the formula (II). The keto compounds of the formula (Ia) given further below are isolated in a generally customary manner.

The reaction according to the invention can also be carried out in a two-phase system, such as, for example, aqueous sodium hydroxide or potassium hydroxide solution/toluene or methylene chloride, if appropriate with the addition of 0.1 to 1 mol of a phase-transfer catalyst, such as, for example, ammonium or phosphonium compounds, benzyldodecyldimethyl-ammonium chloride and triethylbenzyl-ammonium chloride being mentioned as examples.

The optional reduction of the keto compounds of the general formula (Ia)

$$R-\underset{Az}{\underset{|}{CH}}-CO-C(CH_3)_3 \qquad (Ia)$$

to the compounds of the general formula (Ib)

$$R-\underset{Az}{\underset{|}{CH}}-\underset{OH}{\underset{|}{CH}}-C(CH_3)_3 \qquad (Ib)$$

where, in the above formulae (Ia) and (Ib) the symbols R and Az have the meaning given in formula (I), is carried out in a customary manner, such as, for example, by reaction with complex hydrides, if appropriate in the presence of a diluent; or by reaction with aluminum isopropylate in the presence of a diluent; or by reaction with hydrogen in the presence of a catalyst and, if appropriate, in the presence of a diluent.

If complex hydrides are employed, suitable diluents for the reduction reaction are polar organic solvents. These preferably include alcohols, such as methanol, ethanol, butanol or isopropanol, and ethers, such as diethyl ether or tetrahydrofuran. The reaction is carried out in general at 0° to 30° C., preferably at 0° to 20° C. For this purpose, about 1 mol of a complex hydride, such as sodium borohydride or lithium alanate, is employed per mol of the ketone of the formula (Ia). To isolate the reduced compounds of the formula (Ib), the residue is taken up in dilute hydrochloric acid, and the solution is then rendered alkaline and is extracted with an organic solvent. Further working-up is effected in a customary manner.

If aluminium propylate is employed, preferred diluents for the abovementioned reduction are alcohols, such as isopropanol, or inert hydrocarbons, such as benzene. The reaction temperatures can once again be varied within a relatively wide range; in general, the reaction is carried out at between 20° and 120° C., preferably at 50° to 100° C. To carry out the reaction, about 1 to 2 mols of aluminum isopropylate are employed per mol of the ketone of the formula (Ia). To isolate the reduced compounds of the formula (Ib), the excess solvent is removed by distillation in vacuo, and the aluminum compound formed is decomposed with dilute sulphuric acid or sodium hydroxide solution. Further working-up is effected in a customary manner.

If hydrogen is employed, suitable diluents for the reduction to be carried out are polar organic solvents.

These preferably include alcohols, such as methanol and ethanol; and nitriles, such as acetonitrile. The reaction is carried out in the presence of a catalyst. Noble metal catalysts, noble metal oxide catalysts or noble metal hydroxide catalysts, or so-called "Raney catalysts", are preferably used, in particular platinum, platinum oxide and nickel. The reaction temperatures can be varied within a relatively wide range. In general, the reaction is carried out at between 20° and 50° C. The reaction can be carried out under atmospheric pressure, but also under elevated pressure, for example 1 to 2 atm. To carry out the reaction, about 1 mol of hydrogen and 0.1 mol of catalyst are employed per mol of the compound of the formula (Ia). To isolate the reduced compounds of the formula (Ib), the solution is filtered off from the catalyst, and the filtrate is freed from the solvent in vacuo. Further working-up is effected in a customary manner.

The compounds of the formula (I) which can be prepared according to the invention can be converted to acid addition salts or metal salt complexes.

Preferred acids for the preparation of plant-tolerated acid addition salts of the compounds of the formula (I) are the following: hydrohalic acids, such as, for example, hydrochloric acid and hydrobromic acid, in particular hydrochloric acid, and also phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and naphthalene-1,5-disulphonic acid. The acid addition salts of the compounds of the formula (I) can be obtained in a simple manner by customary salt formation methods, for example by dissolving a compound of the formula (I) in a suitable solvent and adding the acid, for example hydrochloric acid, and can be isolated in a known manner, for example by filtration, and if appropriate purified by washing with an inert organic solvent.

Preferred salts for the preparation of metal salt complexes of the compounds of the formula (I) are those of metals of main groups II to IV and of subgroups I and II and IV to VIII, copper, zinc, manganese, magnesium, tin, iron and nickel being mentioned as examples.

Suitable anions of the salts are those which are preferably derived from the following acids: hydrohalic acids, such as, for example, hydrochloric acid and hydrobromic acid and also phosphoric acid, nitric acid and sulphuric acid.

The metal salt complexes of compounds of the formula (I) can be obtained in a simple manner by customary processes, thus, for example, by dissolving the metal salt in an alcohol, for example ethanol, and adding the solution to the compound of the formula (I). Metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating rust fungi, such as, for example, against the brown rust of wheat causative organism (*Puccinia recondita*), against powdery mildew fungi, against further pathogens in cereal cultivation, such as, for example, against the stripe disease of barley causative organism (*Drechslera graminea*), the spot blotch of cereals causative organism *Cochliobolus sations,* the rot blotch of barley causative organism *Pyrenophora teres,* against various pathogens in rice cultivation and against grey mold (*Botrytis cinerea*).

In addition, the active compounds according to the invention also possess a pronounced bactericidal action. The herbicidal action when appropriately high amounts are used should also be mentioned.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl-naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic means, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

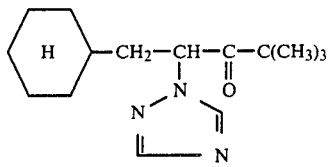

4.8 g of sodium hydride (80% strength suspension in mineral oil, 0.16 mol) are suspended in 50 ml of absolute dimethylformamide, and 26.8 g (0.16 mol) of 3,3-dimethyl-1-(1,2,4-triazol-1-yl)-butan-2-one in 50 ml of absolute dimethylformamide are added dropwise to the stirred suspension at 20° C. to 25° C. After the evolution of hydrogen has ended, 30.8 g (0.17 mol) of bromomethylcyclohexane are added dropwise at 20° C. to 25° C., and the mixture is then heated at 80° C. for 4 hours. After the reaction mixture has cooled, it is poured carefully into 1 liter of water, and the mixture is extracted several times with methylene chloride. The combined organic extracts are dried over sodium sulphate and evaporated down in vacuo. By distilling the residue, 29.5 g (70% of theory) of 1-cyclohexyl-4,4-dimethyl-2-(1,2,4-triazol-1-yl)-pentan-3-one of boiling point 135° C. to 140° C./0.1 are obtained as a slightly yellow-colored oil.

EXAMPLE 2

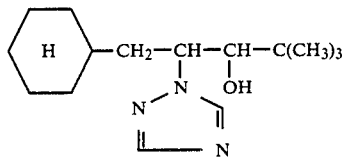

13.2 g (0.05 mol) of 1-cyclohexyl-4,4-dimethyl-2-(1,2,4-triazol-1-yl)-pentan-3-one are dissolved in a mixture of 100 ml of methanol and 20 ml of water, a total of 2 g (0.05 mol) of sodium borohydride is added in several portions, and the mixture is stirred overnight. To work up the reaction mixture, it is brought to pH 5 with dilute hydrochloric acid, and the solvent is evaporated off in vacuo. The residue is taken up in water and extracted several times with methylene chloride. The combined organic extracts are washed with sodium bicarbonate solution and water, dried over sodium sulphate and evaporated down in vacuo. The residue is crystallized using petroleum ether. 10 g (75.2% of theory) of 1-cyclohexyl-4,4-dimethyl-2-(1,2,4-triazol-1-yl)-pentan-3-ol are obtained in the form of colorless crystals of melting point 104° C. to 107° C.

The following compounds of the general formula (I) are obtained in an analogous manner:

$$R-\underset{\underset{Az}{|}}{CH}-A-C(CH_3)_3 \qquad (I)$$

| Example No. | R | Az | A | Physical properties |
|---|---|---|---|---|
| 3 | cyclohexyl-CH₂– | 1,2,4-triazol-1-yl | >C=O | b.p. 120° C./0.1 |
| 4 | cyclohexyl-CH₂– | 1,2,4-triazol-1-yl | >CH–OH | m.p. 138° C. |
| 5 | 2-methylcyclohexyl-CH₂– | 1,2,4-triazol-1-yl | >C=O | b.p. 150° C./0.1 |
| 6 | 2-methylcyclohexyl-CH₂– | 1,2,4-triazol-1-yl | >CH–OH | m.p. 51° C. |
| 7 | 2-methylcyclohexyl-CH₂– | imidazol-1-yl | >C=O | b.p. 160° C./0.2 |
| 8 | 2-methylcyclohexyl-CH₂– | imidazol-1-yl | >CH–OH | m.p. 78° C. |
| 9 | 4-methylcyclohexyl-CH₂– | 1,2,4-triazol-1-yl | >C=O | b.p. 160° C./0.1 |
| 10 | 4-methylcyclohexyl-CH₂– | 1,2,4-triazol-1-yl | >CH–OH | $n_D^{20} = 1.4978$ |
| 11 | 4-methylcyclohexyl-CH₂– | imidazol-1-yl | >CH–OH | oil |
| 12 | cyclopentyl-CH₂– | 1,2,4-triazol-1-yl | >C=O | b.p. 140° C./0.1 |
| 13 | cyclopentyl-CH₂– | 1,2,4-triazol-1-yl | >CH–OH | m.p. 47° C. |

-continued $$R-\underset{\underset{Az}{|}}{CH}-A-C(CH_3)_3 \quad (I)$$

| Example No. | R | Az | A | Physical properties |
|---|---|---|---|---|
| 14 | cyclopentyl-CH₂— with H | 1,2,4-triazol-1-yl | >C=O | m.p. 98° C. |
| 15 | cyclopentyl-CH₂— with H | 1,2,4-triazol-1-yl | >CH—OH | m.p. 127° C. |
| 16 | cycloheptyl-CH₂— with H | 1,2,4-triazol-1-yl | >C=O | $n_D^{20} = 1.5107$ |
| 17 | cycloheptyl-CH₂— with H | 1,2,4-triazol-1-yl | >CH—OH | m.p. 98–104° C. |
| 18 | cycloheptyl-CH₂— with H | 1,2,4-triazol-1-yl | >C=O | $n_D^{20} = 1.5064$ |
| 19 | cycloheptyl-CH₂— with H | 1,2,4-triazol-1-yl | >CH—OH | oil |

USE EXAMPLES

In testing for fungicidal activity, the compounds shown below are employed as comparative substances in the examples which follow:

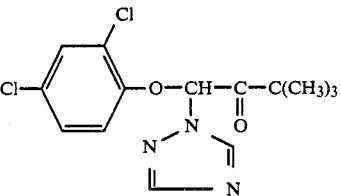

(A)

1-(2,4-Dichlorophenoxy)-3,3-dimethyl-1-(1,2,4-triazol-1-yl)-butan-2-one

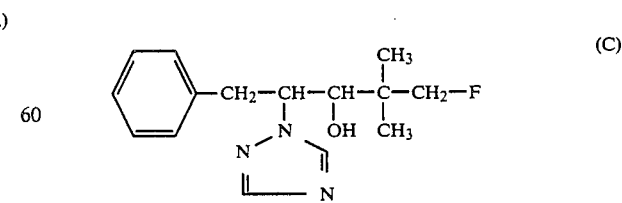

(B) 4,4-Bis-(chloromethyl)-1-phenyl-2-(1,2,4-triazol-1-yl)-pentan-3-one (C) 2,2-Dimethyl-1-fluoro-5-phenyl-4-(1,2,4-triazol-1-yl)-pentan-3-ol

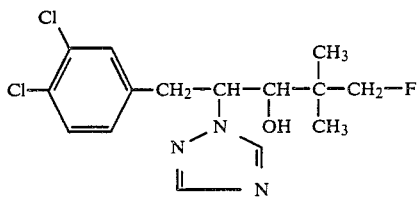 (D)

5-(3,4-Dichlorophenyl)-2,2-dimethyl-1-fluoro-4-(1,2,4-triazol-1-yl)-pentan-3-ol.

EXAMPLE A

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 4 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compound according to the following preparation example: (2).

EXAMPLE B

Puccinia test (wheat)/protective/Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: (2) and (4).

EXAMPLE C

*Drechslera graminea* test (barley)/seed treatment
(syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compound according to the following preparation example: (2).

It will be understood that the specification and examples are illustrative but not limitative of the present invention and that other embodiments within the spirit and scope of the invention will suggest themselves to those skilled in the art.

What is claimed is:

1. A substituted azolylalkyl-t-butyl-carbinol of the formula

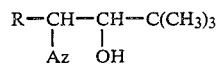

in which

Az is imidazol-1-yl or 1,2,4-triazol-1-yl, and

R is cycloalkyl-alkyl having 3 to 9 carbon atoms in the cyclic moiety and up to 4 carbon atoms in the alkyl and optionally monosubstituted by alkyl having up to 4 carbon atoms, or a plant-tolerated addition product thereof with an acid or metal salt.

2. A compound or addition product according to claim 1, in which R is cyclopropylmethyl, cyclobutylmethyl, cyclopentylmethyl, cyclohexylmethyl or cycloheptylmethyl optionally substituted by methyl or ethyl.

3. A compound according to claim 1 wherein such compound is 1-cyclohexyl-4,4-dimethyl-2-(1,2,4-triazol-1-yl)-pentan-3-ol of the formula

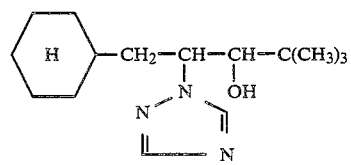

or a plant-tolerated addition product thereof with an acid or metal salt.

4. A compound according to claim 1 wherein such compound is 1-cyclohexyl-4,4-dimethyl-2-(imidazol-1-yl)-pentan-3-ol of the formula

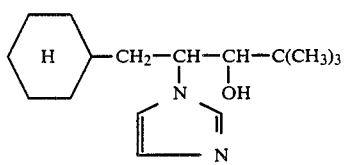

or a plant-tolerated addition product thereof with an acid or metal salt.

5. A fungicidal composition of matter comprising a diluent and a fungicidally effective amount of a compound or a plant-tolerated addition product thereof according to claim 1.

6. A method of combating fungi which comprises administering to such fungi or to a fungus habitat a fungicidally effective amount of a compound or addition product thereof according to claim 1.

7. A method according to claim 6 wherein such compound is
1-cyclohexyl-4,4-dimethyl-2-(1,2,4-triazol-1-yl)-pentan-3-ol or
1-cyclohexyl-4,4-dimethyl-2-(imidazol-1-yl)-pentan-3-ol,
or a plant-tolerated addition product thereof with an acid or metal salt.

* * * * *